United States Patent [19]

Wade et al.

[11] 4,076,823

[45] Feb. 28, 1978

[54] TRIAZOLO-2,4-BENZODIAZEPINES

[75] Inventors: Peter C. Wade, Pennington, N.J.; B. Richard Vogt, Yardley, Pa.; Thomas P. Kissick, Princeton, N.J.

[73] Assignee: E. R. Squibb & Sons, Inc., Princeton, N.J.

[21] Appl. No.: 825,744

[22] Filed: Aug. 18, 1977

[51] Int. Cl.² ............... A61K 31/55; C07D 487/04
[52] U.S. Cl. ............... 424/269; 260/308 R; 260/465 R; 260/465 F; 260/465 G
[58] Field of Search ............... 260/308 R; 424/269

[56] References Cited

U.S. PATENT DOCUMENTS 3,741,957  6/1973  Hester ............... 260/308 R

FOREIGN PATENT DOCUMENTS 2,409,308  9/1974  Germany ............... 260/308 R

Primary Examiner—Alton D. Rollins
Attorney, Agent, or Firm—Lawrence S. Levinson; Merle J. Smith; Burton Rodney

[57] ABSTRACT

Triazolo-2,4-benzodiazepines are provided having the structure

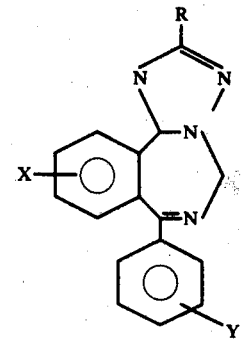

wherein X, Y and R are as defined hereinafter. These compounds have antiinflammatory activity, and sedative, anxiolytic, and muscle relaxant activity. Pharmaceutical compositions containing such compounds and method for using such compounds are also provided.

10 Claims, No Drawings

TRIAZOLO-2,4-BENZODIAZEPINES

The present invention relates to triazolo-2,4-benzodiazepines which are useful as antiinflammatory agents and sedatives and muscle relaxants and to pharmaceutical compositions containing the same, and to methods for using the same.

The triazolo-2,4-benzodiazepines of the invention have the following structure

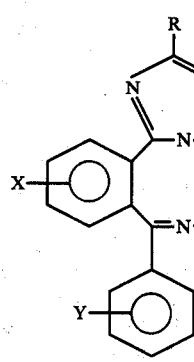

I wherein X is hydrogen, halogen, lower alkyl, lower alkoxy, trifluoromethyl or nitro; Y is hydrogen, halogen, lower alkyl, lower alkoxy, nitro, or trifluoromethyl; R is hydrogen, lower alkyl or trifluoromethyl.

The preferred compounds of the invention are those of formula I wherein X is halogen, Y is hydrogen and R is lower alkyl.

The term "lower alkyl" as used herein refers to alkyl groups having 1 to 4 carbons, with methyl and ethyl being preferred.

The term "lower alkoxy" as used herein refers to lower alkyl groups as defined above attached to an oxygen atom, with methoxy being preferred.

The term "halogen" as employed herein refers to chlorine, bromine, iodine or fluorine, with chlorine and bromine being preferred.

The triazolo-2,4-benzodiazepines of the invention are prepared by reacting a triazoloisoindole of the structure

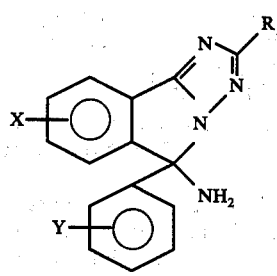

II with hexamethylenetetramine in the presence of a strong acid, such a hydrochloric acid and an inert solvent, such as 1,2-dimethoxyethane (DME) or dioxane to form the formula I triazolo-2,4-benzodiazepines.

The triazoloisoindole starting material of formula II is prepared by reacting a 5-phenyl-1,2,4-triazole of the structure

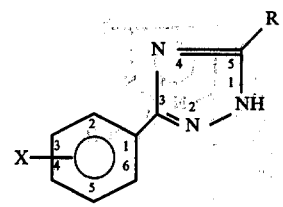

III with a strong base, such as an organometallic base like alkyllithium or aryllithium in the presence of a non-reacting solvent, such as tetrahydrofuran, at temperatures between $-100$ and $+30°$ C. A benzonitrile of the structure

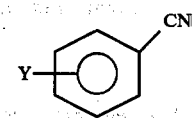

IV is added with stirring and a proton source, such as ammonium chloride, ammonium sulfate, ammonium bromide, dimethylamine hydrochloride or trimethylamine hydrochloride is added to produce the compound of formula II.

The product of the reaction using the formula III compounds wherein X is in the 3-position will yield a mixture of compounds of formula II wherein X is in the 6- or 8- position (of formula II); these compounds may be separated by chromatography or crystallization; such separation is preferably conducted prior to forming the compounds of formula I.

The starting materials of structure III are known in the art or prepared by analogy to known procedures such as according to the procedure outlined in German (East) Patent 67,130 (1969) *Chem. Abstr.* 71, 12441e. Thus, a benzonitrile of the structure

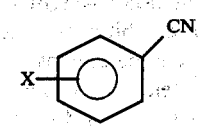

V is condensed with an amino-1,2,4-triazole of the structure

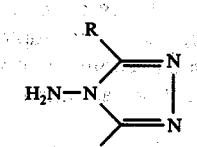

VI in the presence of an alkali metal hydride, such as sodium hydride or lithium hydride, and a non-reacting solvent, such as dimethylsulfoxide (DMSO), or dimethylformamide, to form a compound of the structure

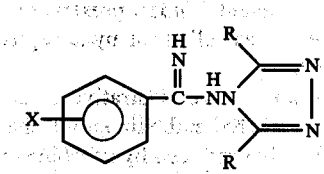

VII which is then reacted with acetic anhydride to form

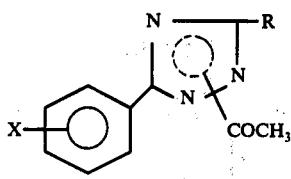

VIII

The acetyltriazole of structure VIII is refluxed in water to form the structure III material.

The starting triazole of structure VI is prepared by techniques well known in the art (e.g., see Th. Curtius and G. M. Dedichen, *J. Prakt. Chem.*, 50, 241 (1894), Beil. 26, 29). Thus, the formula VI compound may be prepared by reaction of hydrazine and an alkylcyanide

R'CN            IX wherein R' is lower alkyl, at temperatures ranging from 100° to 250° C for periods of 0.5 to 48 hours in a sealed vessel, if necessary.

The compounds of formula I have antiinflammatory activity as measured by the reverse passive arthus (RPA) (M. B. Goldlust and W. F. Schreiber, Agents and Actions, 5, 39 (1975)) or other related tests and are useful as antiinflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg to about 150 mg per kg of body weight per day.

The new compounds of the present invention are also capable of modifying the central nervous sytem. When administered to mice, cats, rats, dogs, and other mammalian species in amounts ranging from about 1 mg to about 200 mg per kg of body weight per day, these compounds in particular exhibit central nervous system depressant activity, and can be used as tranquilizers for the relief of anxiety and tension states in the manner of chlordiazepoxide and as sedatives, for example, to promote sleep in anxious or tense subjects. These compounds also exhibit muscle relaxant activity. A preferred dosage regimen for optimum results would be from about 1 mg to about 10 mg per kg of body weight per day, and such dosage units are employed so that a total of from about 35 mg to about 6 g of active ingredient in single or divided doses are administered in a 24 hour period.

For any of these pharmaceutical purposes a compound or mixture of compounds of formula I may be administered orally or parenterally in a conventional dosage form, such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the Centigrade scale.

EXAMPLE 1

9-Chloro-2-methyl-7-phenyl-5H[1,2,4]triazolo-[5,1-a] [2,4]-benzodiazepine

A. 7-Chloro-2-methyl-5-phenyl-5H-[1,2,4]triazolo-[5,1-a]isoindol-5-amine (1) 4-Amino-3,5-4H,1,2,4-dimethyltriazole (Th. Curtius and G. M. Dedichen, *J. Prakt. Chem.*, 50, 241 (1894))

Hydrazine hydrate (100 g, 2.0 mol) and acetonitrile (75 g, 1.8 mol) are placed out in a 1 l. bomb which is sealed and heated at 150° for eight hours. The reaction mixture is heated at 180° (pressure rises to 420 psi) overnight. The bomb is cooled, vented and opened to yield a white solid plus some liquid. The solid is collected on a filter, washed with a small amount of cold water, toluene, and recrystallized from 600 ml ethyl acetate to give 51 g of the title A compound, m.p. 195°14 197°.

(2) 4-Chloro-N-(3,5-dimethyl-4H-1,2,4-triazol-4-yl) benzenecarboximidamide

Sodium hydride [15.32 g (0.364 mol) of a 57% oil dispersion] is washed with ether (X 5) in a sintered glass funnel to remove the oil. The free sodium hydride is washed with a little DMSO into a stirred suspension of 50.0 g (0.363 mol) 4-chlorobenzonitrile and 40.7 g (0.363 mol) 4-amino3,5-4H,1,2,4-dimethyltriazole (prepared in part A (1)) in 200 ml DMSO (distilled from $CaH_2$ under vacuum). After the addition, the mixture is stirred in an ice bath for 1 hour and for 3 hours at room temperature. The reaction mixture is poured into 2 liters of ice water and stirred for 15 minutes until the floculant precipitate coagulates into a filterable state. The product is then filtered out, washed with water, and dried at 50° under vacuum overnight to yield 94.2 g of the title compound, m.p. 303–306°.

The crude triazole (6.0 g) is digested with isopropanol, filtered off and dried to yield 4.1 g of the pure triazole (product), m.p. 310°–312°.

(3) 3-(4-Chlorophenyl)-5-methyl-1H-1,2,4-triazole (H. Becker et al. East German Patent 67,130 (1969), *Chem. Abst.* 71, 124441e))

63.6 g (0.254 mol) of 4-Chloro-N-(3,5-dimethyl-4H-1,2,4-triazol-4-yl)benzenecarboximidamide and 67 ml of acetic anhydride in a 300 ml round bottom flask equipped with a distillation head are heated to 170° in an oil bath. A melt forms from which acetic acid is distilled off. The mixture is refluxed for 2.5 hours and the excess acetic anhydride is removed under vacuum. The residue is triturated with 120 ml of water, and filtered. The filter cake is dissolved in 1 liter of hot absolute ethanol, filtered hot, and the product precipitated from the hot alcohol by adding 3 liters of cold water. The product is filtered off, washed with water and dried at 80° under vacuum to yield: 37.6 g of an N-acetyltriazole m.p. 132°–133°.

27 g (0.114 mol) of the above N-acetyl triazole is refluxed in 800 ml of water for 9 hours (reaction followed by TLC) and stirred overnight at room temperature. The product is filtered out, washed with water, and dried at 90° under vacuum overnight to yield the title A (3) compound, m.p. 173°–175°.

(4) 7-Chloro-2-methyl-5-phenyl-5H[1,2,4]triazolo [5,1-a]isoindol-5-amine 2.0 g (10.3 mmol) of 3-(4-Chlorophenyl)-5-methyl-1H-1,2,4-triazole is dissolved in 50 ml of tetrahydrofuran (THF) (freshly distilled from lithium aluminum hydride) mechanically stirred in a 250 ml round-bottom 3-necked flask equipped with a septum and nitrogen inlet and cooled in an ice bath. 13.6 ml (22.7 mmol) of n-butyllithium (1.67 mol/liter in hexane) is injected with a syringe and the mixture is stirred in the ice bath for 30 minutes. 2.12 g (20.6 mmol) of benzonitrile is added in a little THF. After stirring for 30 minutes in the ice bath, and for 30 minutes at room temperature, the mixture is poured into a chilled stirred mixture of 100 ml of 2.5 M ammonium chloride and 200 ml of chloroform. The layers are separated and the aqueous layer washed with chloroform. The combined chloroform layers are washed with water and dried (Na$_2$SO$_4$). The chloroform is removed under vacuum and the residue is recrystallized from toluene to yield 1.5 g of the title compound, m.p. 173°–175°.

B. 9-Chloro-2-methyl-7-phenyl-5H[1,2,4]triazolo-[5,1-a][2,4]benzodiazepine

To a stirring solution of 3.1 g (10.4 mmol) of 7-chloro-2-methyl-5-phenyl-5H-[1,2,4]triazolo[5,1-a]-isoindol-5-amine and 3.1 g (22 mmol) of hexamethylene-tetramine (hexamine) in 75 ml of DME is added 1.5 ml of 4 N HCl (dioxane). A precipitate forms immediately and the two phase mixture is refluxed. After 5 hours another 1.0 g of hexamine is added and reflux is continued overnight. An additional 1.5 ml of the HCl solution is added after 12 hours and again after an additional 24 hours. After another 24 hours, thin layer chromatography (TLC) shows the disappearance of starting material. The mixture is filtered and the solvent is removed from the filtrate under vacuum. The residue is taken up in CHCl$_3$ and applied to a 5×10 cm silica gel column (Baker 60–200 mesh). The column is eluted with CHCl$_3$ until all of the high R$_f$ material (followed by TLC) is recovered. The solvent is removed in vacuo and the residue recrystallized from 20 ml of acetonitrile to yield 1.3 g of pure product: m.p. 150.5°–152° [concentration of the mother liquor gives an additional 0.2 g for a total yield of 1.5 g (46.6%)].

EXAMPLES 2 to 15

Following the procedure of Example I parts A and B, but substituting for the first benzonitrile, the compound shown in Column I of Table A below, substituting for the amino-triazole, the compound shown in Column II, and substituting for the second benzonitrile, the compound shown in Column III, the compound of the invention shown in Column IV is obtained.

TABLE A

| | Column I | | Column II | | Column III | | Column IV | | |
|---|---|---|---|---|---|---|---|---|---|
| Ex. No. | X (position) | R | Y (position) | | X (position) | R | Y (position) | | |
| 2. | H | CH$_3$ | CH$_3$(2) | | H | | | | |
| 3. | Br(3) | C$_2$H$_5$ | H | | Br(8) | As in Column II | As in Column III | | |
| 4. | CH$_3$(3) | CF$_3$ | C$_2$H$_5$(3) | | CH$_3$(10) | | | | |
| 5. | CH$_3$O(4) | C$_2$H$_5$ | Cl(4) | | CH$_3$O(9) | | | | |
| 6. | CF$_3$(3) | CF$_3$ | CF$_3$(3) | | CF$_3$(8) | | | | |
| 7. | NO$_2$(4) | n-C$_3$H$_7$ | CH$_3$O(2) | | NO$_2$(9) | | | | |
| 8. | H | C$_2$H$_5$ | NO$_2$(3) | | H | | | | |
| 9. | Cl(2) | n-C$_4$H$_9$ | C$_2$H$_5$(2) | | Cl(11) | | | | |
| 10. | C$_2$H$_5$(2) | (CH$_3$)$_2$CHCH$_2$ | t-C$_4$H$_9$(4) | | C$_2$H$_5$(11) | | | | |
| 11. | C$_2$H$_5$O(4) | n-C$_4$H$_9$ | Br(2) | | C$_2$H$_5$O(9) | | | | |
| 12. | NO$_2$(4) | CH$_3$ | Cl(2) | | NO$_2$(9) | As in Column II | As in Column III | | |
| 13. | CF$_3$(4) | C$_2$H$_5$ | H | | CF$_3$(9) | | | | |
| 14. | H | CH$_3$ | H | | H | | | | |
| 15. | H | H | H | | H | | | | |

What is claimed is:

1. A compound of the structure

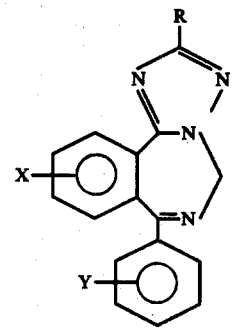

wherein X is hydrogen, halogen, lower alkyl, lower alkoxy, trifluoromethyl or nitro; Y is hydrogen, halogen, lower alkyl, lower alkoxy, trifluoromethyl or nitro; and R is hydrogen, lower alkyl or trifluoromethyl.

2. The compound of claim 1 wherein X is in the 9-position.

3. The compound of claim 2 wherein X is halogen, R is lower alkyl.

4. The compound of claim 1 wherein X is hydrogen, halogen, or lower alkyl.

5. The compound of claim 1 wherein Y is hydrogen, halogen, or trifluoromethyl.

6. The compound of claim 1 wherein R is hydrogen or lower alkyl.

7. The compound of claim 1 having the name 9-chloro-2-methyl-7-phenyl-5H-[1,2,4]triazolo[5,1-a][2,4]-benzodiazepine.

8. A pharmaceutical composition comprising a compound as defined in claim 1 and a physiologically acceptable carrier therefor.

9. A method for treating an inflammatory condition in mammals which comprises administering a therapeutic amount of a composition as defined in claim 8.

10. A method for treating anxiety in mammals, which comprises administering a therapeutic amount of a composition as defined in claim 8.

* * * * *

UNITED STATES PATENT OFFICE
CERTIFICATE OF CORRECTION

Patent No. 4,076,823　　　　　　　　　Dated February 28, 1978

Inventor(s) Peter C. Wade et al.

It is certified that error appears in the above-identified patent and that said Letters Patent are hereby corrected as shown below:

Column 4, line 19, "195°14 197°" should read --195°-197°--.
Column 4, line 27, "4-amino3,5" should read --4-amino-3,5--.

Signed and Sealed this

Twentieth Day of June 1978

[SEAL]

Attest:

RUTH C. MASON
*Attesting Officer*

DONALD W. BANNER
*Commissioner of Patents and Trademarks*